US009061068B2

(12) United States Patent
Kim et al.

(10) Patent No.: US 9,061,068 B2
(45) Date of Patent: Jun. 23, 2015

(54) POLYMERIC NANO-PARTICLES FOR SIRNA DELIVERY USING CHARGE INTERACTION AND COVALENT BONDING

(75) Inventors: Kwang Meyung Kim, Seoul (KR); Ick Chan Kwon, Seoul (KR); Kuiwon Choi, Seoul (KR); Myung Sook Huh, Seoul (KR); Seung Young Lee, Gyeonggi-Do (KR); So Jin Lee, Seoul (KR)

(73) Assignee: KOREA INSTITUTE OF SCIENCE AND TECHNOLOGY (KR)

( * ) Notice: Subject to any disclaimer, the term of this patent is extended or adjusted under 35 U.S.C. 154(b) by 0 days.

(21) Appl. No.: 12/905,212

(22) Filed: Oct. 15, 2010

(65) Prior Publication Data
US 2012/0065242 A1 Mar. 15, 2012

(30) Foreign Application Priority Data

Sep. 10, 2010 (KR) ........................ 10-2010-0089081

(51) Int. Cl.
C07H 21/02 (2006.01)
A61K 47/48 (2006.01)
C12N 15/11 (2006.01)
C12N 15/87 (2006.01)

(52) U.S. Cl.
CPC .......... A61K 47/4823 (2013.01); C12N 15/111 (2013.01); C12N 2310/14 (2013.01); C12N 2310/351 (2013.01); C12N 2320/32 (2013.01); C12N 15/87 (2013.01)

(58) Field of Classification Search
USPC ................... 435/6, 91.1, 91.31, 455, 6.1, 458; 514/1, 2, 44; 536/23.1, 24.5; 977/773, 977/906
See application file for complete search history.

(56) References Cited

U.S. PATENT DOCUMENTS

| 2002/0193331 | A1* | 12/2002 | Boussif et al. | 514/44 |
| 2005/0112187 | A1* | 5/2005 | Meyer | 424/450 |
| 2008/0281041 | A1 | 11/2008 | Rozema et al. | |
| 2010/0130588 | A1* | 5/2010 | Yaworski et al. | 514/44 A |
| 2010/0297756 | A1* | 11/2010 | Adib et al. | 435/366 |
| 2011/0223318 | A1* | 9/2011 | Choi et al. | 427/58 |
| 2011/0305751 | A1* | 12/2011 | Gaillard | 424/450 |
| 2012/0093913 | A1* | 4/2012 | Schreiber et al. | 424/450 |
| 2012/0177723 | A1* | 7/2012 | Torchilin et al. | 424/450 |
| 2013/0149783 | A1* | 6/2013 | Yockman et al. | 435/440 |

OTHER PUBLICATIONS

Huh, M. S., et al., J. Controlled Release, vol. 144, pp. 134-143 (2010).*
Ji et al., FEBS Letters, vol. 552, pp. 247-252 (2003).*
Ji et al., FEBS Lett., vol. 552, pp. 247-252 (2003).*
la Fuente et al, Investigative Ophthalmology & Visual Sci., vol. 49, No. 5, pp. 2016-2024 (2008).*
Issa et al, Drug Discovery Today: Technologies, vol. 2, No. 1, pp. 1-6 (2005).*
Janes et al, Adv. Drug Delivery Rev., vol. 47, pp. 83-97 (2001).*
Kang De Yao et al., J. Appl. Polymer Sci., vol. 48, pp. 343-354 (1993).*
Mao et al, J. Controlled Release, vol. 70, pp. 399-421 (2001).*
Roldo et al, European J. Pharmaceutics and Biopharmaceutics, vol. 57, pp. 115-121 (2004).*
Yoon Yeo et al, J. Biomedical Materials Res., Part A, pp. 668-675 (2006).*
Search Report issued by European Patent Office and received by applicant on Dec. 14, 2011 in connection with corresponding EP patent application No. EP 10 01 3588.
Synthesis and Biological Evaluation of a Bioresponsive and Endosomolytic siRNA-Polymer Conjugate, Martin, et al *Molecular Pharmaceutics, American Chemical Society*, Jun. 1, 2009, vol. 6, No. 3, pp. 752-762, XP002624572.
Down-regulation of PTTG1 by siRNA Suppresses Tumorigenesis and lymph node metastasis of esophageal squamous Cell Carcinoma in vivo, Tetsuo,et al., *Gastroenterology*, vol. 134, No. 4, Suppl.1, Apr. 2008, p. A449, XP0023433895.
Chlorotoxin bound magnetic nanovector tailored for cancer cell targeting, imaging and siNRA delivery, Veiseh, et al., *Biomaterials*, vol. 31, No. 31, Jul. 31, 2010, pp. 8032-8042, XP55014008.
Tumor-homing glycol chitosan/polyethylenimine nanoparticles for the systemic delivery of siRNA in tumor-bearing mice, Huh, et al., *Journal of Controlled Release*, vol. 144, No. 2, Jun. 1, 2010, pp. 134-143, XP55014003.
Office Action issued by the Japanese Patent Office on Mar. 4, 2014 in connection with corresponding Japanese Patent Application No. 2010-232764.
Translation of Office Action issued by the Japanese Patent Office on Mar. 4, 2014 in connection with corresponding Japanese Patent Application No. 2010-232764.
Jong-Ho Kim, et al., *Antitumor Efficacy of Cisplatin-loaded Glycol Chitosan Nanoparticles in Tumor-Bearing Mice*, Journal of Controlled Release, 2008, vol. 127, p. 41-49.
Kyeongsoon Park,et al., *Effect of Polymer Molecular Weight on the Tumor Targeting Characteristics of Self-Assembled Glycol Chits an Nanoparticles*, Journal of Controlled Release, 2007, vol. 122, p. 305-314.

(Continued)

*Primary Examiner* — Jane Zara
(74) *Attorney, Agent, or Firm* — Ostrolenk Faber LLP

(57) ABSTRACT

Disclosed is a polymer-siRNA delivery carrier in which a siRNA is combined with a polymer and the use thereof. More specifically, there is disclosed a stable in vivo polymer-siRNA delivery carrier in which a polymer and a siRNA are combined by using charge interaction and biodegradable covalent bonding at the same time and the use thereof.

The polymer-siRNA delivery carrier in which a polymer and a siRNA are combined by using charge interaction and biodegradable covalent bonding at the same time has a high siRNA deliver efficiency to a target portion in vivo. Hence, according to the polymer-siRNA binder, the siRNA for treatment can be effectively delivered to a target portion such as in vivo cancer tissue, and the like even with administration of a relatively low concentration, and thus widely used for the treatment of various kinds of diseases.

9 Claims, 5 Drawing Sheets

(56) References Cited

OTHER PUBLICATIONS

So Jin Lee, et al., *Tumor Specificity and Therapeutic Efficacy of Photosensitizer-Encapsulated Glycol Chitosan-based Nanoparticles in Tumor-Bearing Mice*, Elssevier Biomaterials, May 2009, vol. 30, p. 2929-2939.

*Stability and Cellular Uptake of Polymerized siRNA (poly-siRNA)/polyethylenimine (PEI) Complexes for Efficient Gene Silencing*. Seung-Young Lee,etal., J.Control, Release, Feb. 2010, vol. 141, p. 339-346.

*Thiolated Trimethyl Chitosan Nanocomplexes as Gene Carriers with High in Vitro and in Vivo Transfection Efficiency*, Xin Zhao, et al.. J. Control. Release., May 2010, vol. 144, p. 46-54.

*Thiolated Chitosan/DNA Nanocomplexes Exhibit Enhanced and Sustained Gene Delivery*, Dongwon Lee, et al., Pharm. Res., 2006, vol. 24, No. 1, p. 157-167.

*Intracellular siRNA Delivery System Using Polyelectrolyte Complex Micelles Prepared From VEGF siRNA-PEG Conjugate & Cationic Fusogenic Peptide*, Soo Hycon Lee,etal, Biochem. Biophys.Res. Commun., 2007, vol. 354, p. 511-516.

*Synthesis and Biological Evaluation of a Bioresponsive and Endosomolytic siRNA-Polymer Conjugate*, Martin Meyer, et al., Mol. Pharm., 2009, vol. 6, No. 3, p. 752-762.

*Nanoparticles of Glycol Chitosan and its Thiolated Derivative Significantly Improved the Pulmonary Delivery of Calcitonin*, Abdullah Makhlof, et al., Int. J. Pharm., Jul. 7, 2010, vol. 397, p. 92-95.

Office Action issued by Japanese Patent Office on Mar. 5, 2013 in connection with corresponding Japanese application No. 2010-232764 and English translation thereof.

* cited by examiner

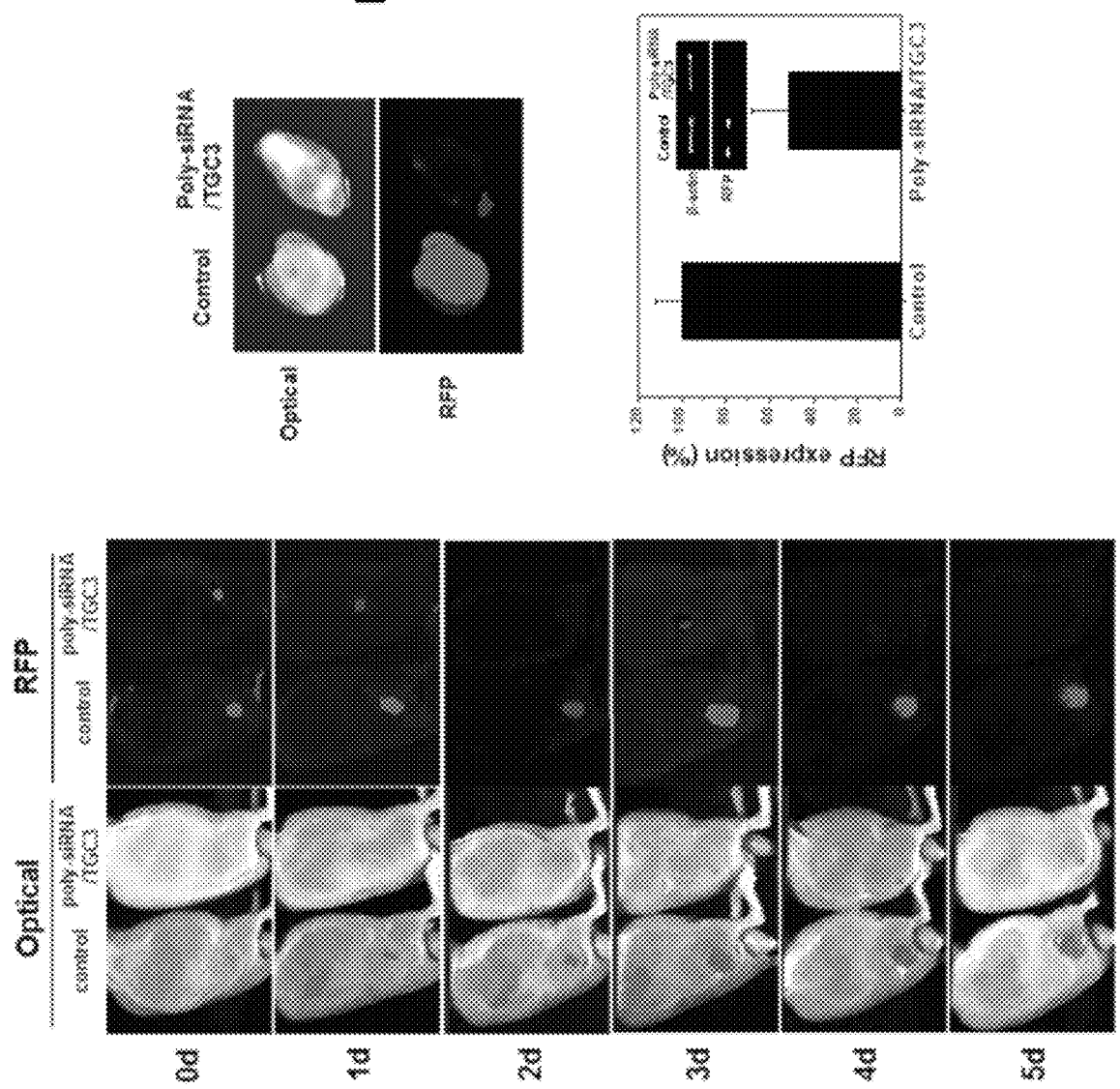

POLYMERIC NANO-PARTICLES FOR SIRNA DELIVERY USING CHARGE INTERACTION AND COVALENT BONDING

RELATED APPLICATION

Pursuant to 35 U.S.C. §119(a), this application claims the benefit of earlier filing date and right of priority to Korean Application No. 10-2010-0089081, filed on Sep. 10, 2010, the contents of which is incorporated by reference herein in its entirety.

BACKGROUND OF THE INVENTION

1. Field of the Invention

The present invention relates to a polymer-siRNA delivery carrier in which a siRNA is combined with a polymer and the use thereof. More specifically, the present invention relates to stable polymer-siRNA nanoparticles in which a polymer and a siRNA are combined by using charge interaction and bio-degradable covalent bonding at the same time and the use thereof.

2. Background Art

In recent years, the core technology of gene therapy depends on how oligonucleotide having strong negative charge is delivered into a desired tissue. In general, live cells have a very low permeability to high molecular weight molecules such as proteins or oligonucleotides. Since only some low molecular weight materials can enter the cytoplasm or nucleus within cells through the membrane of live cells at a very low rate, thereby causing a limitation when delivering high molecular weight molecules containing proteins or oligonucleotides. In order to overcome such a limitation, studies on various gene delivery carriers and their delivery method have been carried out. One of them is a delivery method using various viruses. The delivery method using viruses is excellent in the aspect of delivery efficiency but has a problem in applying to clinics due to an effect on the gene expression function of a host by virus genes and its carcinogenic possibility. Accordingly, it is required the development of delivery carriers for allowing stable gene delivery in the body while maintaining a high transfection efficiency of viruses.

RNA interference (RNAi) is primarily used in the gene therapy field as a treatment showing a prominent effect in reducing the expression of a specific gene. Due to its high activity and precise gene selectivity, siRNA is expected to be an alternative treatment to antisense oligonuceotide (ODN) currently being used as a therapeutic agent as a result of the past 20-year's research. Accordingly, more than thirty pharmaceutical and bio technology companies have concentrated on the development of a treatment drug based on siRNA. Particularly, the development of siRNA-related treatments for treating diabetes, obesity, rheumatism, Parkinson's disease, B/C-type hepatitis, AIDS, and cancer is in progress.

siRNA, which is a short, double-stranded RNA consisting of about 19 to 23 nucleotides, suppresses the expression of a gene by targeting the mRNA of a target gene having a complementary base sequence to them. In other words, an mRNA regulating the expression metabolic process of a specific gene is singularly degraded to stop the protein synthesis of the target gene, thereby treating a disease. Accordingly, studies on delivery carriers using cationic liposomes or micelles and cationic polymers for delivering siRNA having strong negative charge into a living body have been carried out. siRNA has a low stability and thus it is degraded in a short period of time by a variety of enzymes existing in plasma in large quantities in vivo. Particularly, in case of an injection treatment, it is more quickly destroyed if not stably treated chemically, and difficult to easily permeate membranes having negative charge due to its cationic property, and as a result, the transmissivity into cells is reduced, thereby causing a problem that the treatment efficiency is rapidly reduced. Although siRNA consists of double strands, the binding of ribose sugars constituting a RNA is very unstable chemically compared to the binding of deoxyribose sugars constituting a DNA, and thus most of them are rapidly degraded in vivo with a half-life of around 30 minutes. Furthermore, siRNA is recognized as foreign substances in vivo, thereby causing adverse effects on an immune system. Moreover, siRNA affects other portions of the gene that is not an originally planned portion of the gene, thereby causing cross-hybridization in a gene base sequence.

Accordingly, it is important to develop delivery carriers capable of neutralizing negative charge to allow in vivo permeation while overcoming the shortcoming of such siRNA in which treatment efficiency is rapidly reduced due to its low stability that is easily degraded in vivo. Preferably, the siRNA delivery carrier as a treatment has a singular accumulation in the internal circulation and specific disease portion, and should be suitably bio-degraded in the body. Glycol chitosan, which is one of bio-derived polymers, has been already known for the superiority as an anti-cancer delivery carrier due to its biocompatibility and biodegradability, and excellent cancer singular accumulation. Our laboratory has developed a siRNA delivery carrier (glycol chitosan-PEI) supplemented with positive charge by adding polyethyleneimine (PEI) strongly coupled with nucleotide to glycol chitosan (Korean Patent No. 2009-0041428). However, the cohesion is insufficient with the charge of a polymer alone in forming an effective composite with siRNA having strong negative charge.

On the other hand, there have been efforts for increasing the molecular weight of siRNA itself to complement the weak in vivo stability of low molecular weight siRNA, thereby allowing effective coupling with polymer delivery carriers. The Jean-Paul Behr group has reported that in vivo delivery efficiency of siRNA is increased by using sticky siRNA produced by adding DNA sequence to the 3' end of siRNA (Proceedings of the National Academy of Sciences of the United States of America, 2007. 104 (41): 16050-16055), and our laboratory has released as a patent and a paper that in vivo stability and gene expression effect are increased by producing poly-siRNA in which a thiol group is introduced at the 5' end of siRNA to increase the size by a disulfide bond between siRNAs (Korean Patent No. 10-2009-0042273, Journal of Controlled release, 2010. 141 (3): 339-346). Besides, for a method of producing poly-siRNA in which the size is increased to secure stability, there has been reported that the expression of a target gene is suppressed if a disulfide bond is introduced as a cross-linker to produce multimeric siRNA (Nature materials, 2010. 9: 272-278).

Hence, the present inventor has produced a polymer-siRNA delivery carrier in which a polymer having excellent biocompatibility and a siRNA are connected by charge interaction as well as biodegradable covalent bonding to increase the in vivo stability and delivery efficiency to a target portion of the siRNA that can be used as an effective gene treatment. Specifically, it has been developed a polymer-siRNA delivery carrier, which is a novel nano delivery carrier applicable to various disease treatments, by connecting a siRNA, poly-siRNA or multimeric siRNA to a polymer having suitable positive charge and containing a functional group using charge interaction as well as covalent bonding to a functional group at the end of siRNA, thereby blocking the expression of a specific protein of disease cells.

SUMMARY OF THE INVENTION

The present disclosure is contrived to solve the foregoing problem, and an object of the present invention is to provide a novel siRNA delivery carrier or a drug composition containing the siRNA delivery carrier capable of enhancing the in vivo stability of siRNA and enhancing the delivery efficiency of siRNA.

In order to accomplish the foregoing objective, the present disclosure provides a siRNA delivery carrier in which a polymer and a siRNA are combined by using charge interaction and biodegradable covalent bonding at the same time.

In addition, the present disclosure provides a drug composition containing a polymer-siRNA delivery carrier.

In a siRNA delivery carrier according to the present invention, a polymer and a siRNA are combined by using charge interaction and biodegradable covalent bonding at the same time, thereby stably delivering the siRNA to the cell or tissue of a targeted disease. Accordingly, it is useful because siRNAs are selectively accumulated at a target portion to block the expression of a specific disease protein.

The siRNA delivery carrier according to the present invention may be applicable to cancers and other disease models, and thus can be used as a treatment for treating a wide range of diseases.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings:

FIG. 7 is an experimental result of gene expression suppression effect to the mouse cancer tissue of a poly-siRNA-TGC composite with the method of Example 5. It is illustrated a view in which the expression of RFP, which is a model target protein by a poly-siRNA-TGC composite, is drastically reduced.

DETAILED DESCRIPTION OF THE INVENTION

Figure 1:
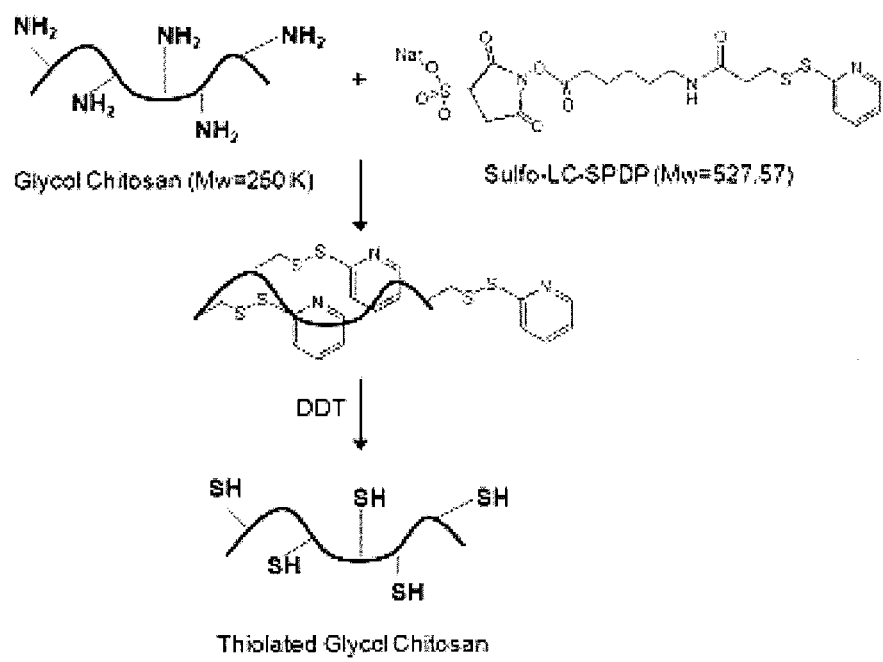
FIG. 1 illustrates a schematic diagram in which —SH (thiol group) is introduced to glycol chitosan having an amine using a cross-linker to produce thiolated glycol chitosan (TGC) in Example 1.

Hereinafter, the present disclosure will be described in detail.

The present disclosure provides a siRNA delivery carrier produced by combining a polymer with a siRNA to effectively deliver the siRNA in vivo, wherein the siRNA delivery carrier is characterized in that a polymer and a siRNA are combined by using charge interaction and biodegradable covalent bonding at the same time.

A polymer-siRNA delivery carrier according to the present invention is produced by combining a polymer with various types of siRNAs, wherein their binding is carried out by using charge interaction and biodegradable covalent bonding, and the structure may be shown as follows.

A-B (A: a polymer, B: various types of siRNAs)

In the above, "A" is a polymer having charge and functional group. Specifically, all polymers having biocompatibility may be used, and particularly, anyone having positive charge and functional group at the same time, which is selected from chitosan, glycol chitosan, protamine, polylysin, polyarginine, polyethyleneimine, dextran, hyaluronic acid, albumin, and their derivatives, can be used with no limitation. For the synthetic polymer, PEI (Polyethylenimine), PLGA (poly lactic glycolic acid), poly-L-lysine, and the like can be used, but it is not necessarily limited to them.

In the above, "B" may be various kinds of siRNAs such as a monomer siRNA or high molecular siRNA (poly siRNA, multimer siRNA). Preferably, the siRNA may be 15 to 30 nucleotide monomer siRNAs, or a multimer siRNA consisted of 100 to 400 nucleotides, which is its polymer. The strand of siRNA may be preferably selected between molecular weights 10,000 and 1,000,000. For the sequence of the siRNA, it may be preferably used a sequence, such as VEGF (vascular endothelial growth factor), NF-kB, heat shock protein, heat shock factor, and the like for the purpose of treatment can be used, but it is not necessarily limited to this. In the following example, a siRNA base sequence to RFP (red fluorescence protein) was used to check the delivery efficiency of siRNA with is fluorescence.

The "A" and "B" are connected by using charge interaction and biodegradable covalent bonding. The charge interaction is a charge interaction between a siRNA having negative charge and a polymer having positive charge. The method of physically combining a siRNA with the outside of an amphiphillic polymeric nanoparticles has the maximum load of 95%, which is very high compared to a case where the maximum load of chemical binding is limited to 10%.

The biodegradable bonding may be selected from disulfide bond, ester bond, anhydride bond, hydrazone bond, enzyme-specific peptide bond, and the like, but it is not necessarily limited to this. Such biodegradable bonding can be degraded under a specific bio-environment. The biodegradable bonding between a polymer and a siRNA according to the present invention, which is biodegraded by various enzymes, acidities, and the like in a bio-environment, allows the suppression of target gene expression by siRNA separated out due to the degradation between the siRNA and polymer when degraded by a specific enzyme, or the like in vivo. For instance, if a thiol group is introduced at an end of siRNA and an end of polymer as a functional group for biodegradable covalent bonding, then the siRNA and polymer form a biodegradable bonding referred to as a disulfide bond. If the siRNA and polymeric nanoparticles having the disulfide bond are introduced in vivo, then siRNA may be reduced and separated out by glutathione (GSH) existing in vivo. Particularly, considering a report that the concentration of glutathione (GSH) increases in cancer cells, it is seen that biodegradable bonding such as disulfide bond in a polymer-siRNA nanoparticle delivery carrier according to the present invention can be effectively biodegraded to deliver siRNA to a target portion.

If the binding of a polymer and a siRNA is performed by charge interaction alone, then the cohesion is insufficient, thereby limiting the range of polymers that can be used in combination with siRNA. Also, there is a problem that it is unstable in vivo and separated prior to reaching the purposed place. However, a siRNA delivery carrier according to the present invention is more excellent because the polymer and siRNA are combined by chemical biodegradable covalent bonding as well as charge interaction, thereby more enhancing biocompatibility and stably delivering siRNA to a target portion.

The production of a siRNA delivery carrier according to the present invention by combining a polymer (A) with a siRNA (B) may be implemented by the following method, comprising the steps of:

(a) introducing a functional group for biodegradable covalent bonding to a polymer having positive charge;

(b) introducing or activating a functional group at one end or both ends of siRNA, and (c) stably combining a polymer produced in the step (a) with a siRNA produced in the step (b) through charge interaction and biodegradable covalent bonding to produce nanoparticles.

In the above method, the steps may be also implemented at the same time according to the binding scheme. The polymeric nanoparticles produced by the foregoing method may effectively form a composite with various types of siRNAs in aqueous solution to form a nano-sized self-assembly, and may be selectively accumulated in a specific disease portion (for example, vascularized target EPR, cancer, rheumatism, inflammatory disease). Preferably, the size of a polymer-siRNA delivery carrier according to the present invention, produced as described above, may be 10 to 2000 nm, and the molecular weight thereof may be $10^3$ to $10^7$ Da.

On the other hand, a siRNA delivery carrier according to the present invention may be used as an effective ingredient of a pharmaceutical composition. Accordingly, the present invention provides a pharmaceutical composition containing an effective dose of polymer-siRNA delivery carriers.

The pharmaceutical composition according to the present invention may include one of more kinds of pharmaceutically acceptable carriers in addition to the siRNA delivery carrier according to the present invention for administration.

The pharmaceutically acceptable carriers should be compatible with an effective ingredient of the present invention, and may be used by mixing with one or more ingredients of saline solution, sterilized solution, Ringer's solution, buffered saline, dextrose solution, malto-dextrin solution, glycerol, ethanol, and their ingredients. As occasion demands, other typical additives, such as antioxidant, buffer solution, bacteriostatic agent may be added thereto. In addition, diluent, dispersant, surfactant, binder and lubricant may be added thereto to be formulated as an injectable formulation such as aqueous solution, suspension, emulsion, and the like.

Also, it may be formulated in various types such as powder, tablet, capsule, liquid, injectable, ointment, syrup or the like, and may be provided as a unit-dose or multi-dose container, for example, sealed ampoules, bottles, etc.

Pharmaceutical compositions according to the present invention may be orally or parenterally administered. The route of administration of pharmaceutical compositions according to the present invention may not be limited to them, but for example, oral, intravenous, intramuscular, arterial, intramedullary, intradural, intracardiac, transdermal, subcutaneous, intraperitoneal, secretary, sublingual, or topical administration may be also used. For clinical treatments, such pharmaceutical compositions according to the present invention may be formulated as a suitable drug formulation using the prior art. For example, when administered orally, it may be mixed with an inert diluent or edible carrier, or sealed in a hard or soft gelatin capsule, or pressed as a tablet. For oral administration, active compound may be mixed with an excipient to be used as an intake tablet, buccal tablet, troche, capsule, elixir, suspension, syrup, wafer, or the like. In addition, various formulations such as injectable and parenteral administration may be produced by using publicly or commonly known technologies in the art.

The dose of the composition according to the present invention may vary depending on patient's body weight, age, gender, health status, diet, administration time, administration method, excretion rate, and severity of disease, and may be easily determined by an expert in the art.

Example 1

Introduction of Thiol Group to Hydrophilic Polymer, Glycol Chitosan

Although glycol chitosan has no bio toxicity and effectively accumulated in cancer tissue, glycol chitosan itself has weak positive charge, thereby not allowing effective charge interaction with siRNA. Thus, a glycol chitosan derivative having a pyridyldithiol-activated amine group was formed by using a heterobifunctional cross linker, sulfo-LC-SPDP.

30 mg of glycol chitosan (molecular weight 250 kDa) was dissolved in 10 is ml of pH 7.4 phosphate buffer, and then reacted with 1, 2, and 5 mg of sulfo-LC-SPDP (molecular weight 527.57 Da, 2, 5, and 10% to amine group of glycol chitosan), respectively, at room temperature for a day. Then, 4, 9, and 18 mg of DTT (dithiothreitol) each were added thereto, and reacted for three hours, and then the pH of each solution was decreased to 3 or 4. Then, it was dialyzed for 24 hours by using a dialysis membrane having a cut-off of 12,000 Da to remove unreacted sulfo-LC-SPDP and DTT, and then freeze-dried (FIG. 1).

Example 2

Bonding of Glycol Chitosan Polymer with Polymerized Oligonucleotide which Having Thiol Group The stability and amount of negative charge of a polymerized poly-siRNA having a thiol group was increased, and applied to thiol-introduced hydrophilic polymer glycol chitosan (TGC) to form a composite by using charge interaction and disulfide bond at the same time.

Figure 2:
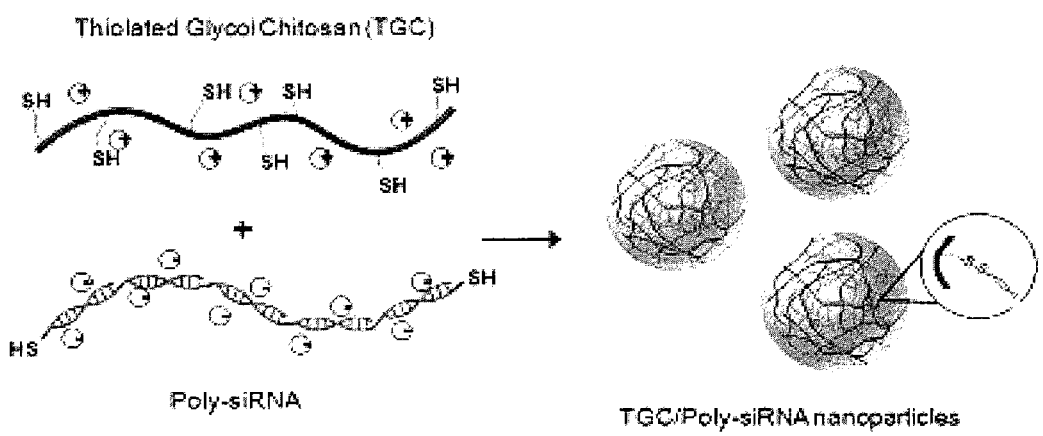
FIG. 2 illustrates a schematic diagram in which both end groups react a poly-siRNA containing a SH (thiol group) with thiolated glycol chitosan (TGC) to form a composite by disulfide bond and electrical interaction in Example 2.
Figure 3:
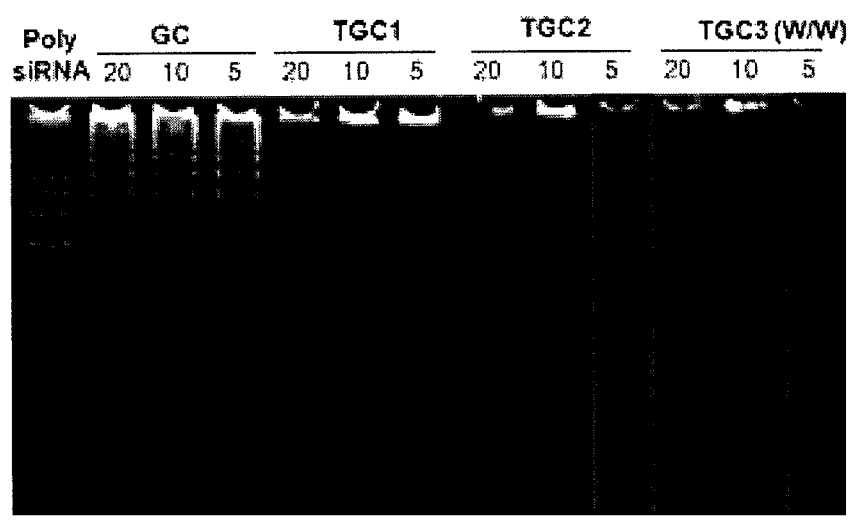
FIG. 3 illustrates whether or not a composite is formed by reacting a poly-siRNA in Example 2 with TGC having a different level of glycol chitosan or thiol group introduction.
Figure 4:
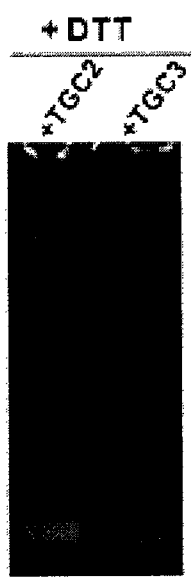
FIG. 4 is a view in which dithiothreitol (DTT) is treated and electrophoresis is carried out to check whether or not there exists a binding between poly-siRNA-TGC produced by the method of Example 2 as illustrated in FIG. 2.

50 μg of poly-siRNA (10 mM HEPES, 1 mM EDTA, pH 8.0) and 250 μg of glycol chitosan polymer (TGC) having a thiol group were dissolved and mixed in 100 μL of HEPES buffer (10 mM, 1 mM EDTA, pH8.0) and then reacted at 37° C. for one hour to form a stable composite (FIG. 2). In FIG. 3, it is illustrated that binding is not formed by pure glycol chitosan alone without introducing poly-siRNA and functional group, and whether or not a composite with poly-siRNA is formed according to a level of SH group substitution of TGC (2%: TGC1, 5%: TGC2, and 10%: TGC3) when forming the composite between poly-siRNA and TGC. Poly-siRNA and TGC were mixed with various weight ratios and reacted at 37° C. for one hour and then electrophoresis was carried out in 8% acrylamide gel at 150 V for 35 minutes Syber-gold staining was done to check TGC-poly-siRNA complex formation and extra poly-siRNAs that had not been reacted with composite formation using gel documentation equipment. Also, DTT was processed at 37° C. for three hours to check that it was due to disulfide bond, and electrophoresis was carried out as described above to confirm that it was reduced to a monomolecular weight siRNA (FIG. 4).

Example 3

Verification of Gene Expression Suppression Effect by Delivering a Composite of Thiol Group-Introduced Glycol Chitosan Polymer and Polymerized Oligonucleotide (Poly-siRNA)

Figure 5:
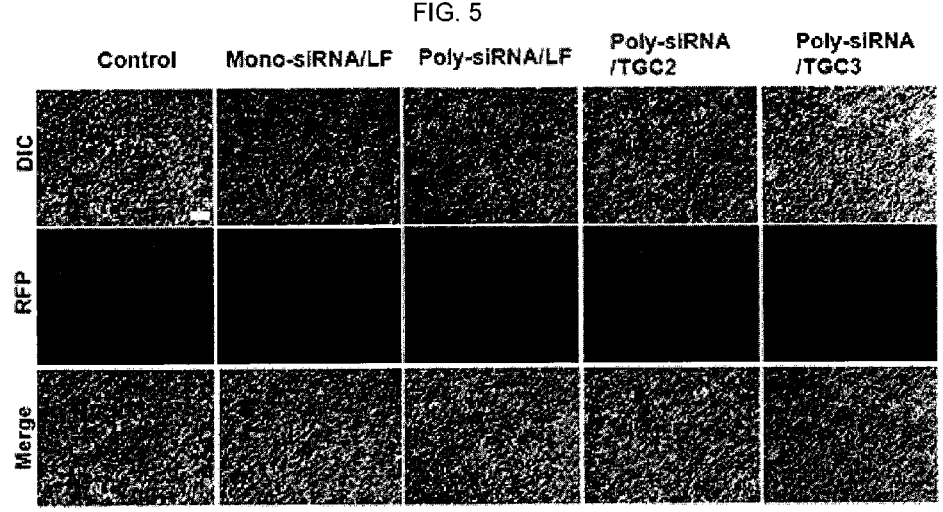
FIG. 5 is a photo illustrating a result of gene expression suppression effect in a cell by composite nanoparticles produced using a poly-siRNA produced in Example 3 and TGC (TGC2, TGC3, weight ratio 5:1)

Composite nanoparticles produced by poly-siRNA and TGC (TGC2, TGC3, 5:1 weight ratio) were treated in a RFP-expressed melanoma cell line, RFP-B16/F10 ($1.2*10^5$/dish) cells, to be a siRNA concentration of 50 nM with a control group (control, mono-siRNA/LF, poly-siRNA/LF), and then after 24 hours, a RFP expression suppression efficacy was obtained with a RFP fluorescence microscopic image. In this experiment, siRNA to red fluorescent proteins (RFPs) was produced and used, and the LF of mono-siRNA/LF and poly-siRNA/LF denotes Lipofectamine™ 2000 from Invitrogen (FIG. 5). Poly-siRNA delivery by TGC was found to be effective in RFP gene expression suppression.

Example 4

Figure 6:
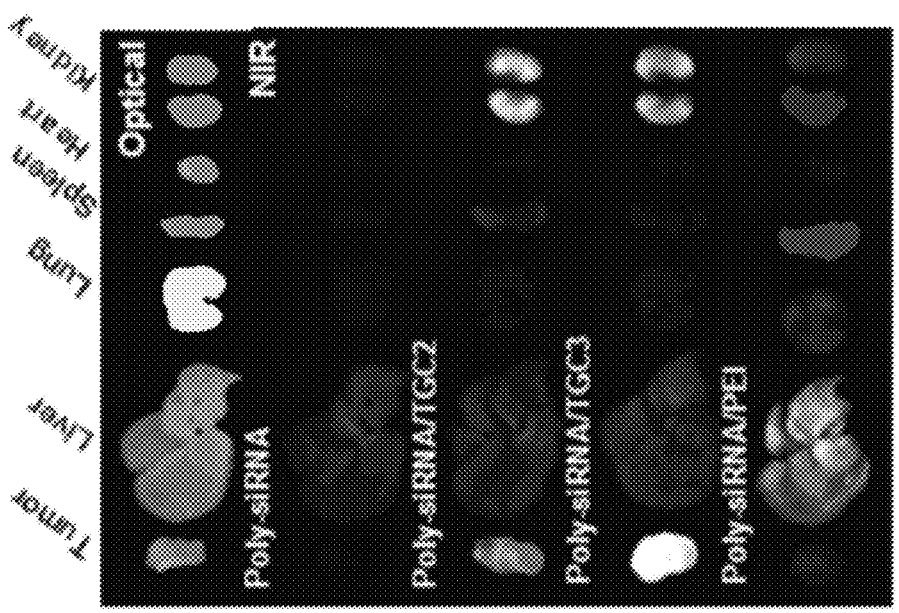
FIG. 6 is a view illustrating the accumulation of poly-siRNA-TGC upon tissue and time-based circulation in a mouse of a poly-siRNA-TGC composite produced by using poly-siRNA modified by a near-infrared fluorescent material (Cy 5.5) with the method of Example 4.

Mouse Tissue Distribution and Tumor Targeting Test of Thiol Group-Introduced Glycol Chitosan Polymer and Polymerized Oligonucleotide (Poly-siRNA) Composite A poly-siRNA-TGC composite made by using poly-siRNA modified with a near-infrared fluorescent material (Cy 5.5) was injected into a tail vein of mice transplanted with SCC7 cancer cells, and then the in vivo circulation of the material was observed hourly through noninvasive optical imaging. Singular accumulation in cancer cells was confirmed in case of Cy5.5-labeled poly-siRNA constituting a composite with TGC compared to poly-siRNA or poly-siRNA-PEI injected without carrier TGC, and especially, it was confirmed that tumor targeting and internal preservation are most excellent in the experimental group in which composites are made with TGC3 (FIG. 6).

Example 5

Gene Expression Suppression Effect Test by Delivering Thiol Group-Introduced Glycol Chitosan Polymer and Polymerized Oligonucleotide (Poly-siRNA) Composite with an Animal Experiment $1\times10^6$ RFP-B16/F10 melanoma cell lines were injected into a lower portion of dorsal waist in a nude mouse to make an animal cancer model, and poly-siRNA-TGC3 composites were injected into a tail vein two times (day 0 and day 2) in a two-day interval since RFP fluorescence was detected in the mouse through an optical device to compare the RFP expression effect in cancer tissue by poly-siRNA delivered through the blood vessel. FIG. 7 illustrates a view in which RFP expression in cancer tissue is drastically reduced when injecting a poly-siRNA-TGC composite. Also, when cancer tissue was excised to extract total RNAs in the cancer tissue on the 6th day and the RFP expression amount in the tissue was compared by using reverse transcription-polymerase chain reaction, it was confirmed an effective expression reduction in the mouse tissue injected with poly-siRNA-TGC3.

As described above, a new formulated siRNA delivery carrier having a polymer-siRNA nanoparticle type connected and produced by using charge interaction and biodegradable bonding at the same time through the present invention can form nanoparticles in aqueous solution and stably deliver siRNA to a target portion, thereby enhancing the treatment efficiency by siRNA.

As a result, a polymer-siRNA delivery carrier according to the present invention has an advantage that can be applied to various cancer and disease models.

What is claimed is:

1. A polymer-siRNA delivery carrier with the following structure in which a polymer (A) and a siRNA (B) are connected by using charge interaction and biodegradable covalent bonding at the same time:

A-B wherein, "A" is chitosan or glycol chitosan as a polymer having positive charge and functional group, and "B" is a poly-siRNA in which a plurality of siRNAs are connected by biodegradable covalent bonding having a functional group at one end or both ends of the poly-siRNA.

2. The polymer-siRNA delivery carrier of claim 1, wherein the siRNA (B) has a form having a functional group for being connected to a polymer at one end or both ends thereof.

3. The polymer-siRNA delivery carrier of claim 1, wherein the siRNA (B) poly-siRNA consisting of 100 to 400 nucleotides.

4. The polymer-siRNA delivery carrier of claim 1, wherein the polymer (A) and siRNA (B) are connected by using charge interaction and biodegradable covalent bonding at the same time, and its in vivo stability is more increased compared to a case where the polymer and siRNA are connected by only using charge interaction.

5. The polymer-siRNA delivery carrier of claim 1, wherein the biodegradable covalent bonding between the polymer (A) and siRNA (B) is selected from disulfide bond, ester bond, anhydride bond, hydrazone bond, and enzyme-specific peptide bond.

6. The polymer-siRNA delivery carrier of claim 1, wherein the size of the polymer-siRNA delivery carrier is 10 to 2000 nm.

7. The polymer-siRNA delivery carrier of claim 1, wherein the molecular weight of the polymer-siRNA delivery carrier is $10^3$ to $10^7$ Da.

8. A polymer-siRNA delivery carrier, wherein the polymer-siRNA delivery carrier in claim 1 is used for treating a cancer.

9. An anti-cancer composition, comprising an effective dose of the polymer-siRNA delivery carrier in claim 1.

* * * * *